US00PP25298P3

(12) United States Plant Patent
Glen

(10) Patent No.: US PP25,298 P3
(45) Date of Patent: Feb. 24, 2015

(54) NECTARINE TREE NAMED 'PEARLICIOUS XXII'

(50) Latin Name: *Prunus persica*
Varietal Denomination: Pearlicious XXII

(71) Applicant: Lowell Glen, Le Grand, CA (US)

(72) Inventor: Lowell Glen, Le Grand, CA (US)

( * ) Notice: Subject to any disclaimer, the term of this patent is extended or adjusted under 35 U.S.C. 154(b) by 70 days.

(21) Appl. No.: 13/694,610

(22) Filed: Dec. 13, 2012

(65) Prior Publication Data

US 2014/0173790 P1 Jun. 19, 2014

(51) Int. Cl.
*A01H 5/00* (2006.01)

(52) U.S. Cl.
USPC ..... Plt./188

(58) Field of Classification Search
CPC ..... A01H 5/0856; A01H 5/00; A01H 5/08
USPC ..... Plt./188, 189
See application file for complete search history.

(56) References Cited

U.S. PATENT DOCUMENTS

PP14,242 P2 10/2003 Bradford
PP22,758 P2 5/2012 Bradford

*Primary Examiner* — June Hwu

(57) ABSTRACT

The present invention relates to a new and distinct variety of nectarine tree, *Prunus persica*, broadly characterized by a medium size, moderately vigorous, hardy, self-fertile, productive and regular bearing tree. The variety blooms during the mid season and requires about 525 chilling hours. The fruit matures under the ecological conditions described in late May, with first picking on May 24, 2012. The fruit is uniformly medium in size, globose in shape, semi-freestone in type, firm and melting in texture, white in flesh color, virtually full red in skin color, and a tasty balance of light acid and sugar in flavor.

1 Drawing Sheet

Botanical classification: *Prunus persica.*
Variety denomination: 'PEARLICIOUS XXII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of nectarine tree, which has been denominated varietally as 'Pearlicious XXII'.

In 2003 I made a first generation hybridization using '6P740' (unpatented) yellow flesh nectarine as the selected seed parent and 'Diamond Pearl' (U.S. Plant Pat. No. 14,242) white flesh nectarine as the selected pollen parent. The fruit of this cross was gathered that spring and the seeds were removed from the fruit, stratified, germinated, and grown as seedlings on their own root in my greenhouse. Upon reaching dormancy that winter, the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its pollen parent, 'Diamond Pearl' (U.S. Plant Pat. No. 14,242) nectarines by producing white flesh nectarines that are sub-acid, sweet, firm, medium size with bitter kernels, but is quite distinguished therefrom by having globose instead of reniform leaf glands and by producing fruit that is semi-freestone instead of clingstone and that matures about twelve days earlier.

The present variety is most similar to 'Pearlicious I' (U.S. Plant Pat. No. 22,758) nectarine by being self-fertile and producing white flesh nectarines that are nearly full red in skin color, firm in texture, sweet in flavor, and about the same size, but is distinguished therefrom by requiring more chilling hours, by blooming later, by having globose instead of reniform leaf glands, and by producing fruit that is semi-freestone instead of clingstone in type, that has more acid, that has a bitter instead of sweet kernel, and that ripens about three days earlier.

SUMMARY OF VARIETY

In summary, the present nectarine variety is characterized by a medium size, moderately vigorous, hardy, self-fertile, productive and regular bearing tree. The variety blooms during the mid season and requires about 525 chilling hours. The fruit matures under the ecological conditions described in late May, with first picking on May 24, 2012. The fruit is uniformly medium in size, globose in shape, semi-freestone in type, firm and melting in texture, white in flesh color, virtually full red in skin color, and a tasty balance of light acid and sugar in flavor.

DRAWING

The accompanying photograph consists of four whole fruits positioned to display the characteristics of the skin color and form, one divided fruit to reveal the flesh and stone, a clean dry stone, two insets to reveal buds and blossoms, a typical tip shoot, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of full ripe on Jun. 2, 2012, on the original tree during its ninth growing season. The blossom and flower descriptions were made the previous blooming season. All major color code designations are by reference to the Inter-Society Color Council, National Bureau of Standards. Common color names are also used occasionally.

Parentage

Seed parent: '6P740' (unpatented) nectarine.

Pollen parent: 'Diamond Pearl' (U.S. Plant Pat. No. 14,242) nectarine.

Tree

Size: Medium, reaching and maintaining a height of 10' [3.05 m.] and a spread of 8' [2.44 m.] after nine growing seasons utilizing typical dormant pruning.

Vigor: Moderately vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Approximate chilling requirement: 525 hours.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

- *Size.*—Medium, reaching a maximum diameter of 4" [101.6 mm.] after the ninth growing season.
- *Texture.*—Shaggy.
- *Bark color.*—A Strong brown [55. s.Br] and Brownish gray [64. brGy] variegation with Moderate yellowish brown [77. m.yBr] crevices.
- *Lenticels.*—Approximate Number Per Square Inch: 8. Color: Moderate orange yellow [71. m.OY]. Average Size: 3/8" [9.5 mm.]. Shape: Eye-shaped, elongated.

Branches:

- *Size.*—Diameter of limb is 2½" [63.5 mm.] measured 12" above the crotch, 1⅜" [34.9 mm.] measured 12" above the first fork.
- *Texture.*—Smooth on first year wood, increasing roughness with age.
- *Color.*—1st Year Wood Topside: Grayish red [19. gy.R]. 1st Year Wood Underside: Brilliant yellow green [116. brill.YG]. Second Year Wood: Strong brown [55. s.Br].
- *Lenticels.*—Number Per Square Inch: About 45 on second year wood. Color: Light grayish yellowish brown [79. l.gy.yBr]. Average size: 1/16" [1.6 mm.] on second year wood. Shape: Eye-shaped, elongated.

Leaves:

- *Size.*—Medium. Average Length: 5⅛" [130.2 mm.]. Average Width: 1⅝" [41.3 mm.].
- *Arrangement.*—Alternate.
- *Thickness.*—Medium.
- *Form.*—Elliptical.
- *Apex.*—Acuminate.
- *Base.*—Acute to rounded.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: 5/16" [7.9 mm.]. Average Thickness: 1/16" [1.6 mm.]. Surface Texture: Smooth. Color: Very yellow green [115. v.YG].
- *Stipules.*—Number: Usually 2 per leaf, up to 6 per growing tip. Average Length: 3/8" [9.5 mm.]. Surface Texture: Smooth. Color: Brilliant yellow green [116. brill.YG] becoming Deep reddish brown [41. deep rBr] with maturity.
- *Glands.*—Number: 1 to 6 per leaf. Position: Most are alternately positioned on the petiold and base of blade. Size: Small, typically 1/64" [0.4 mm.] in diameter. Form: Globose. Color: Brilliant yellow green [116. brill.YG] becoming Moderate reddish brown [43. m.rBr] with age.
- *Leaf buds.*—Pointed, medium in size.

Flower buds:

- *Hardiness.*—Hardy, with respect to central California winters.
- *Diameter.*—Typically 3/8" [9.5 mm.] 1 week before bloom.
- *Length.*—Typically 5/8" [15.9 mm.] 1 week before bloom.
- *Form.*—Not appressed.
- *Surface.*—Pubescent.
- *Tip color.*—Moderate purplish pink [250. m.pPk].

Flowers: Perfect, complete, perigynous, usually a single pistil, about thirty stamens, five sepal and petal locations alternately positioned.

- *Type.*—Showy, large.
- *Average flower diameter.*—1⅞" [47.6 mm.].
- *Number of petals.*—Mostly five, extra petal fragments or double blossoms are occasionally observed.
- *Petal shape.*—Circular to oval.
- *Petal margin.*—Entire, slightly wavy.
- *Average petal diameter.*—¾" [19.1 mm.].
- *Average petal length.*—¾" [19.1 mm.].
- *Petal apex.*—Rounded.
- *Petal base.*—Rounded to somewhat truncate.
- *Petal color.*—Light purplish pink [249. l.pPk] toward the apex, Deep purplish pink [248. deep pPk] toward the base on both sides.

*Anther color.*—Strong red [12. s.R] over a Light yellow [86. l.Y] center at bloom onset.
*Pollen.*—Anthers produce an abundance of Brilliant yellow {83. brill.Y} pollen.
*Stigma color.*—Pale yellow green [121. p.YG].
*Stigma position.*—Typically located about ⅛" [3.2 mm.] above the anthers.
*Ovary.*—Non-pubescent.
*Sepal color.*—Dark purplish red [259. d.pR] on the outer surface.
*Sepal length.*—¼" [6.4 mm.].
*Sepal width.*—5/32" [4.0 mm.].
*Sepal apex.*—Rounded to elliptical to match the sepal length and width.
*Sepal margin.*—Fairly smooth.
*Average pistil length.*—¾" [19.1 mm.].
*Average stamen length.*—9/16" [14.3 mm.].
*Fragrance.*—Moderate.
*Blooming period.*—Medium, with 'Spring Bright' (U.S. Plant Pat. No. 7,507) nectarine.
*Onset of bloom.*—One percent on Feb. 19, 2012.
*Date of full bloom.*—Feb. 28, 2012.
*Duration of bloom.*—One to two weeks, dependent on ambient temperature.
*Number per cluster.*—1 to 3 with single flowers most common.

Fruit

Maturity when described: Full ripe, Jun. 2, 2012.
Date of first picking: May 24, 2012.
Date of last picking: Jun. 2, 2012.
Size: Uniform, Medium.
*Average diameter axially.*—2⅝" [66.7 mm.].
*Average diameter across cheek plane.*—2 13/16" [71.5 mm.].
*Average diameter across suture plane.*—2 13/16" [71.5 mm.].
*Typical weight.*—7.0 ounces [199 grams].
Form: Uniform, globose, slightly compressed axially.
*Longitudinal section form.*—Slightly elliptical.
*Transverse section through diameter.*—Round.
Suture: An inconspicuous line located in a shallow groove, that extends from the base to just past the pistil point.
*Near the base.*—A shallow sharp groove.
*Along the side.*—A shallow trough.
*Near the apex.*—A shallow groove.
Ventral surface: Rounded, lipped stronger toward the apex.
Lips: Slightly unequal.
Cavity: Flaring, slightly elongated in the suture plane, suture showing on both sides, Yellowish white [92. yWhite] stem markings typical.
*Depth.*—7/16" [11.1 mm.].
*Breadth.*—1 1/16" [27.0 mm.].
Base: Slightly truncate, cordate if viewed parallel to the suture.
Apex: Rounded, sometimes cordate if viewed parallel to the suture.
Pistil point: Apical, negligible in length, depressed within the suture.
Stem: Medium.
*Average length.*—⅜" [9.5 mm.].
*Average width.*—3/16" [4.8 mm.].

Skin:
*Thickness.*—Medium.
*Surface.*—Smooth.
*Tenacity.*—Tenacious to flesh.
*Astringency.*—Non-astringent.
*Tendency to crack.*—Slight in wet season.
*Color.*—Dark red [16. d.R] over a Strong red [12. s.R] background with areas of Pale pink [7. p.Pk] where protected from sunlight.
Flesh:
*Color.*—White [263. White], with some Moderate red [15. m.R] to Grayish red [19. gy.R] flecking toward the skin.
*Surface of pit cavity.*—Covered with Greenish white [153. gWhite] to Pinkish white [9. pkWhite] broken fibers when twisted from the stone.
*Amygdalin.*—Scarce.
*Juice.*—Moderate, rich.
*Texture.*—Medium, crisp, melting.
*Fibers.*—Abundant, fine.
*Ripens.*—Slightly earlier at the apex.
*Flavor.*—A tasty balance of light acid and sugar, typically 16 to 18 brix.
*Aroma.*—Slight.
*Eating quality.*—Very good.

Stone

Type: Semi-freestone.
Form: Oval.
Hilum: Narrow.
Base: Slightly oblique.
Apex: Acuminate.
Sides: Equal.
Surface: Irregularly furrowed toward the apex, pitted toward the base.
Ridges: Rounded.
External color: Dark orange yellow [72. d.OY].
Pit wall color when cracked: Pale orange yellow [73. p.OY].
Cavity surface color: Strong yellowish brown [74. s.yBr].
Average pit wall thickness: ¼" [6.4 mm.].
Average width: 1⅛" [28.6 mm.].
Average length: 1½" [38.1 mm.].
Average breadth: ⅝" [15.9 mm.].
Tendency To split: Slight.
Kernel:
*Form.*—Oval.
*Skin color.*—Dark orange yellow [72. d.OY] when first removed.
*Pellicle color.*—Dark yellowish brown [78. d.yBr].
*Vein color.*—Dark yellowish brown [78. d.yBr].
*Taste.*—Bitter.
*Viable.*—Yes, using embryo culture techniques.
*Average width.*—½" [12.7 mm.].
*Average length.*—¾" [19.1 mm.].
*Amygdalin.*—Scant.

Use

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Pearlicious I' (U.S. Plant Pat. No. 22,758) nectarine by being self-fertile and producing white flesh nectarines that are nearly full red in skin color, firm in texture, sweet in flavor, and about the same size, but is distinguished therefrom by requiring more chilling hours, by blooming later, by having globose instead of reniform leaf glands, and by producing fruit that is semi-freestone instead of clingstone in type, that has more acid, that has a bitter instead of sweet kernel, and that ripens about three days earlier.

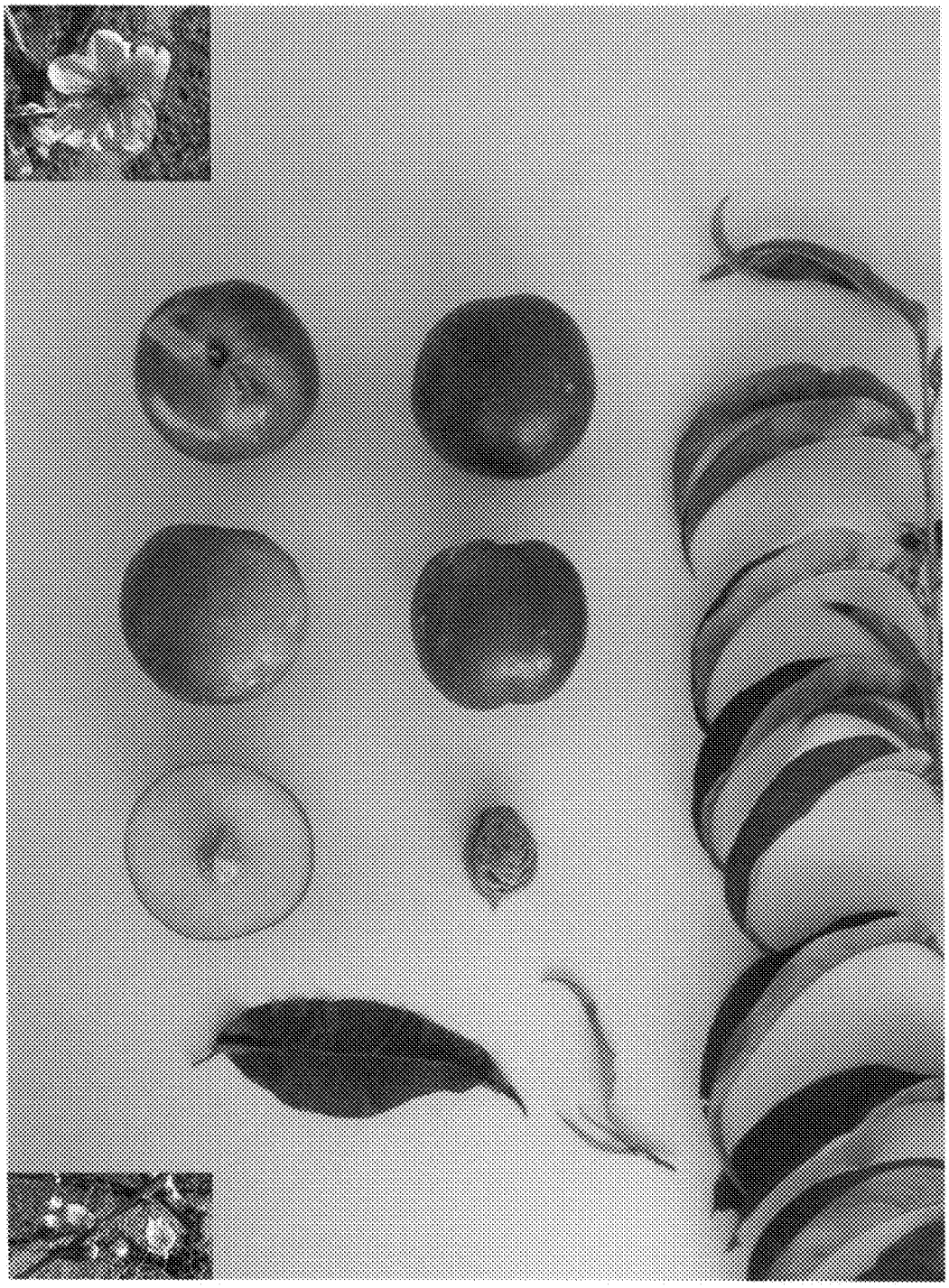

* * * * *